United States Patent
Sasaki et al.

(10) Patent No.: US 9,850,266 B2
(45) Date of Patent: Dec. 26, 2017

(54) PHOSPHORYLCHOLINE GROUP-CONTAINING COMPOUND AND PHOSPHORYLCHOLINE COMPLEX

(71) Applicant: NOF Corporation, Tokyo (JP)

(72) Inventors: Takashi Sasaki, Kanagawa (JP); Takanori Fujita, Kanagawa (JP); Norio Iwakiri, Kanagawa (JP); Nobuyuki Yamamoto, Kanagawa (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/519,746

(22) PCT Filed: Oct. 13, 2015

(86) PCT No.: PCT/JP2015/078862
§ 371 (c)(1),
(2) Date: Apr. 17, 2017

(87) PCT Pub. No.: WO2016/060096
PCT Pub. Date: Apr. 21, 2016

(65) Prior Publication Data
US 2017/0240576 A1 Aug. 24, 2017

(30) Foreign Application Priority Data

Oct. 15, 2014 (JP) ................................. 2014-210546
Oct. 15, 2014 (JP) ................................. 2014-210547

(51) Int. Cl.
*C07F 9/572* (2006.01)
*C07F 9/12* (2006.01)
*C07K 14/76* (2006.01)

(52) U.S. Cl.
CPC .............. *C07F 9/5725* (2013.01); *C07F 9/12* (2013.01); *C07K 14/76* (2013.01)

(58) Field of Classification Search
CPC .................................. C07F 9/5725; C07F 9/12
See application file for complete search history.

(56) References Cited

U.S. PATENT DOCUMENTS 5,455,032 A 10/1995 Kenny et al.
2008/0175852 A1 7/2008 Rezanka

FOREIGN PATENT DOCUMENTS

| FR | 1551060 | * 11/1968 | ................ C07F 9/09 |
|---|---|---|---|
| FR | 1551060 A | 12/1968 | |
| JP | 2007-119643 A | 5/2007 | |
| WO | WO-03/036297 A1 | 5/2003 | |
| WO | WO-2004/074298 A1 | 9/2004 | |
| WO | WO-2005/100405 A2 | 10/2005 | |
| WO | WO-2009/128348 A1 | 10/2009 | |

OTHER PUBLICATIONS

Lindsay, Thomas J. et al., The Preparation of Stable Phosphorylcholine-Erythrocyte Conjugates for Use in Plaque Assays, *Journal of Immunological Methods*, Sep. 16, 1983, 62(3):373-379, Elsevier Science Publishers B.V.

Tanaka, Norimitsu et al., Intranasal immunization with phosphorylcholine induces antigen specific mucosal and systemic immune responses in mice, Vaccine, Mar. 30, 2007, 25(14):2680-2687, Elsevier Ltd.

International Search Report in International Application No. PCT/JP2015/078862, filed Oct. 13, 2015.

* cited by examiner

*Primary Examiner* — Joseph R Kosack
(74) *Attorney, Agent, or Firm* — Saliwanchik, Lloyd & Eisenschenk

(57) ABSTRACT

[Object] To provide a phosphorylcholine group-containing compound capable of producing a phosphorylcholine complex, and the phosphorylcholine complex, the phosphorylcholine complex being easily manufactured and suitable for use as a phosphorylcholine antigen.

[Solving Means] There are provided a phosphorylcholine group-containing compound having a structure represented by the following formula (1), and a phosphorylcholine-protein complex having a structure in which the phosphorylcholine group-containing compound and an amino acid amine site of a protein are amide bonded.

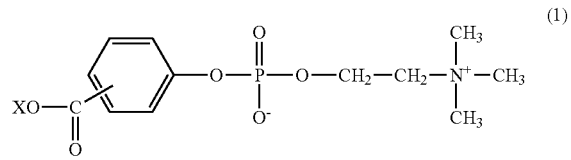

(1)

(X represents a hydrogen atom, a monovalent cation residue, or a hydroxysuccinimide group).

4 Claims, 9 Drawing Sheets

PHOSPHORYLCHOLINE GROUP-CONTAINING COMPOUND AND PHOSPHORYLCHOLINE COMPLEX

CROSS-REFERENCE TO RELATED APPLICATIONS

This application is the U.S. national stage application of International Patent Application No. PCT/JP2015/078862, filed Oct. 13, 2015, which claims priority to Japanese Application Nos. 2014-210546 and 2014-210547, filed Oct. 15, 2014, the disclosures of each of which are incorporated herein by reference in their entirety.

TECHNICAL FIELD

The present invention relates to a phosphorylcholine group-containing compound and a phosphorylcholine complex.

BACKGROUND ART

Phosphorylcholine (PC) is a main component of not only an inflammatory phospholipid such as a platelet-activating factor or an oxidized low density lipoprotein but also an immunogenic component of many bacteria including *Streptococcus pneumoniae*. A compound containing a PC group is used as a PC antigen for the purpose of production of a PC specific antibody. For example, in Patent Literature 1, an example where a PC antigen is used in immunization treatment of atherosclerosis is disclosed. Atherosclerosis is a chronic disease that causes a thickening of the innermost layer (the intima) of large and medium-sized arteries. Atherosclerosis is the major cause of cardiovascular disease including myocardial infarction. Blood flow is decreased in affected areas in atherosclerosis, and ischemia and tissue destruction may be caused in organs supplied by the affected vessel.

According to Patent Literature 1, it is indicated that a monoclonal antibody with specificity to PC and a composition thereof are obtained by using, as a PC antigen, a PC-protein conjugate obtained by boding an immunological carrier protein to PC, and the PC specific monoclonal antibody and the composition thereof are effective in immunization treatment of atherosclerosis. Further, in Patent Literature 2, use of a PC antigen as a vaccine for inducing immunoprotection against infections by *Streptococcus pneumoniae* or the like is disclosed. Other examples of the study aimed at such a vaccine include Non-Patent Literature 1. In Non-Patent Literature 1, it has been reported that a PC antibody titer is increased by administering a PC-protein conjugate in the presence of an immunopotentiating agent in an animal experiment.

Further, although various methods of introducing a phosphorylcholine group into a molecule to form a polymer complex have been proposed (e.g., Patent Literatures 3 and 4), a PC-protein complex based on a phosphorylcholine group-containing compound has not been developed. This is mainly because a manufacturing process therefor needs a reaction of a plurality of stages and it is not easily manufactured due to the structure for a phosphorylcholine group-containing compound to express its function. Therefore, a PC group-containing compound that is easily manufactured and functions as a PC-protein complex is desired.

CITATION LIST

Patent Literature

Patent Literature 1: WO 2005/100405
Patent Literature 2: U.S. Pat. No. 5,455,032
Patent Literature 3: Japanese Unexamined Patent Application Publication No. 2007-119643
Patent Literature 4: WO 2004/074298

Non-Patent Literature

Non-Patent Literature 1: Norimitsu T. et. al., "Vaccine", 2007, 25(14), p. 2680-2687.

SUMMARY OF INVENTION

Problem to be Solved by the Invention

As described above, it is an object of the present invention to provide a phosphorylcholine group-containing compound capable of producing a phosphorylcholine complex, and the phosphorylcholine complex, the phosphorylcholine complex being easily manufactured and suitable for use as a phosphorylcholine antigen.

Means for Solving the Problem

The present inventors have extensively studied to solve the above-mentioned problems. As a result, the present inventors have found that a compound having a compact structure in which an aromatic carboxylic acid structure is in a molecule can unexpectedly solve the above-mentioned problems, and have completed the present invention.

Specifically, the present invention is the following [1] to [4].

[1] A phosphorylcholine group-containing compound having a structure represented by the following formula (1).

[Chem. 1]

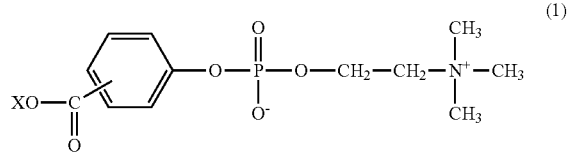

(X represents a hydrogen atom, a monovalent cation residue, or a structure represented by the following formula (2))

[Chem. 2]

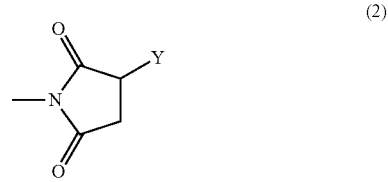

(Y represents a hydrogen atom or $SO_3Na$)

[2] A phosphorylcholine-protein complex having a structure in which a phosphorylcholine group-containing compound having a structure represented by the following formula (1') and an amino acid amine site of a protein are amide bonded.

[Chem. 3]

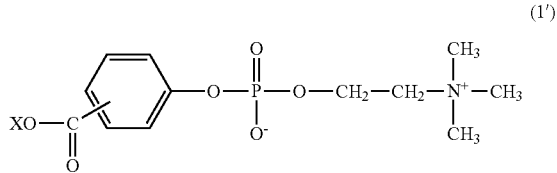

(1')

(X represents a hydrogen atom or a monovalent cation residue)

[3] A phosphorylcholine-peptide complex having a structure in which a phosphorylcholine group-containing compound having a structure represented by the following formula (1') and an amino acid amine site of an oligopeptide are amide bonded.

[Chem. 4]

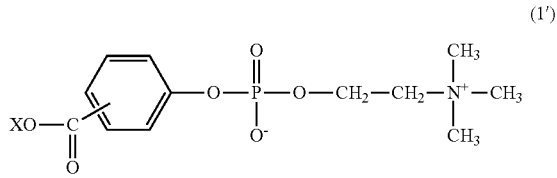

(1')

(X represents a hydrogen atom or a monovalent cation residue)

[4] A phosphorylcholine-amino acid complex having a structure in which a phosphorylcholine group-containing compound having a structure represented by the following formula (1') and an amino acid amine site of an amino acid are amide bonded.

[Chem. 5]

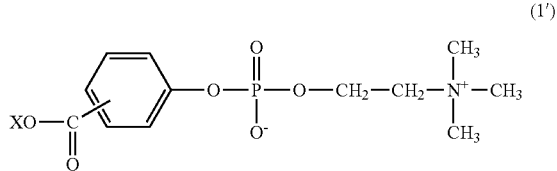

(1')

(X represents a hydrogen atom or a monovalent cation residue)

Advantageous Effects of Invention

It is possible to provide a phosphorylcholine group-containing compound capable of producing a phosphorylcholine complex, and the phosphorylcholine complex, the phosphorylcholine complex being easily manufactured and suitable for use as a phosphorylcholine antigen.

MODE(S) FOR CARRYING OUT THE INVENTION

1. Phosphorylcholine (PC) Group-Containing Compound

Figure 1:
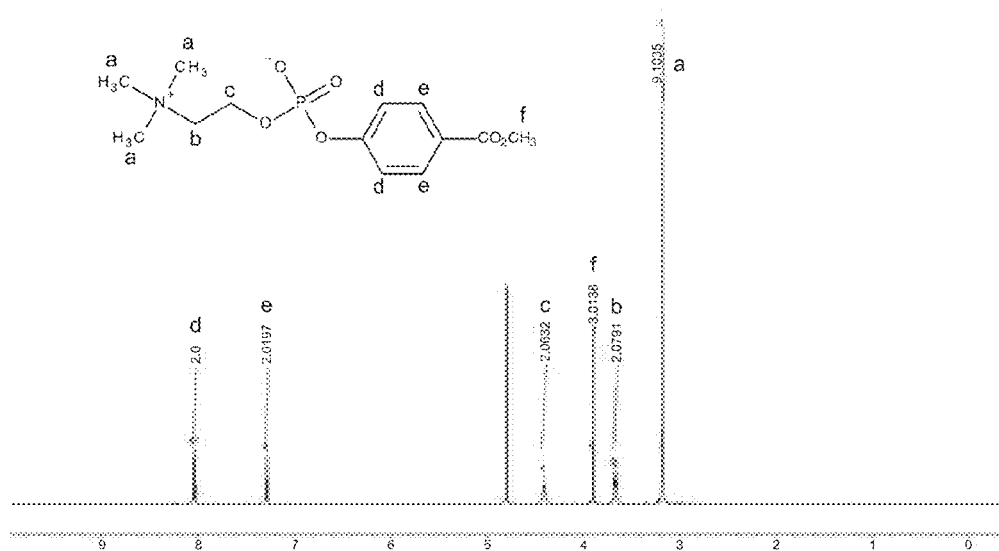
FIG. 1 A $^1$H NMR spectrum of 4-methoxycarbonylphenyl phosphorylcholine.

A phosphorylcholine group-containing compound according to the present invention has a structure represented by the following formula (1).

[Chem. 6]

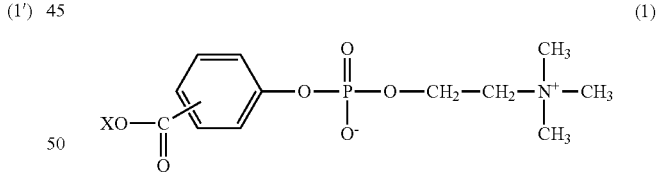

(1)

(X represents a hydrogen atom, a monovalent cation residue, or a structure represented by the following formula (2))

[Chem. 7]

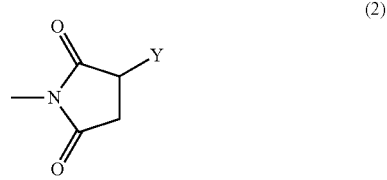

(2)

(Y represents a hydrogen atom or SO$_3$Na)

Examples of the above-mentioned monovalent cation residue include, but particularly not limited to, an alkali metal such as lithium, sodium, and potassium, and a nitrogen-containing organic compound in which ammonia, imidazole, dimethylaminopyridine, triethylamine, diazabicyclooctane, diazabicyclononene (DBN), diazabicycloundecene (DBU), or the like is protonated.

Further, when X is hydroxysuccinimide having a structure represented by the above-mentioned formula (2), it is more advantageous for causing the amidation reaction to advantageously proceed as an activated carboxyl group to achieve a PC complex. Hydroxysuccinimide is amidated immediately before desorbing. Further, although the —COOX group in the formula (1) is bonded to any one of carbons in the benzene ring, it is favorably bonded to a para-position to the phosphorylcholine group.

A PC group-containing compound according to the present invention has a structure in which one PC group and one carboxyl group are bonded to a benzene ring. Specifically, since it has one carboxyl group in a molecule, a cross-linking reaction does not occur when it is bonded to a protein, oligopeptide, or amino acid. Accordingly, it is possible to achieve a water-soluble PC-protein complex, PC-peptide complex, or PC-amino acid complex, which is suitable for use as a PC antigen, by using the PC group-containing compound according the present disclosure as a raw material of a PC complex.

2. Method of Manufacturing PC Group-Containing Compound

The PC group-containing compound according to the present invention can be manufactured by the following manufacturing method 1 or 2.

Manufacturing Method 1:

By hydrolyzing a compound having a structure represented by the following formula (3) by using a basic compound, a compound having a structure that contains a carboxyl group and is represented by the formula (1) is produced.

[Chem. 8]

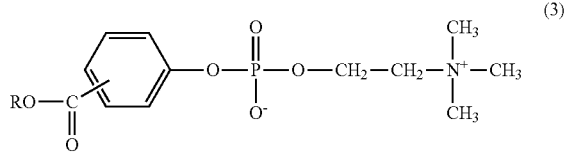
(3)

(R represents a $C_1$ to $C_6$ alkyl group or a benzyl group)

Manufacturing Method 2:

By oxidizing a compound having a structure represented by the following formula (4) by using an oxidizing agent, a compound having a structure that contains a carboxyl group and is represented by the formula (1) is produced.

[Chem. 9]

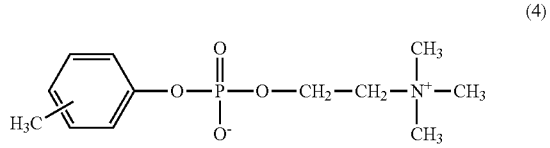
(4)

<Manufacturing Method 1 for PC Group-Containing Compound>

A manufacturing method 1 for a PC group-containing compound specifically includes the following processes A1 to A3.

Process A1: By causing a carboxylate ester-containing phenolic compound and 2-chloro-2-oxo-1,3,2-dioxaphospholane (COP) to react in a solvent by using a dehydrochlorination agent, a carboxylate ester-containing oxaphospholane (OP) compound is generated.

Process A2: By causing the carboxylate ester-containing OP compound obtained in the process A1 to react with trimethylamine, a carboxylate ester-containing PC compound is generated.

Process A3: By hydrolyzing the ester of the carboxylate ester-containing PC compound obtained in the process A2 in the presence of a basic compound in water, a compound having a structure that contains a carboxyl group and is represented by the formula (1) is produced.

(Process A1)

The process A1 is a process in which a carboxylate ester-containing OP compound is generated by causing a carboxylate ester-containing phenolic compound and COP to react in a solvent by using a dehydrochlorination agent. As the above-mentioned carboxylate ester-containing phenolic compound, for example, a compound having a structure in which one carboxylate ester is bonded to a benzene ring, such as an oxybenzoic acid ester, can be used. In addition, any of ortho-, meta-, and para-positional isomers thereof can also be used. Examples of the above-mentioned oxybenzoic acid ester include methyl esters (methyl hydroxybenzoate), ethyl esters (ethyl hydroxybenzoate), propyl esters (propyl hydroxybenzoate), butyl esters butyl hydroxybenzoate), pentyl esters (pentyl hydroxybenzoate), hexyl esters (hexyl hydroxybenzoate), and benzyl esters (benzyl hydroxybenzoate). Further, the above-mentioned oxybenzoic acid ester is favorably, for example, a para-oxybenzoic acid ester such as methyl para-hydroxybenzoate, ethyl para-hydroxybenzoate, propyl para-hydroxybenzoate, butyl para-hydroxybenzoate, and benzyl para-hydroxybenzoate in view of the availability or economy.

The process A1 can be performed in the presence of a solvent. As the solvent, a non-protic solvent is favorable. Examples of the non-protic solvent include nitriles such as acetonitrile, ketones such as acetone and methylethylketone, amides such as dimethylformamide, esters such as ethyl acetate and isopropyl acetate, ethers such as tetrahydrofuran, and chlorine-based organic solvents such as chloroform and dichloromethane. In the process A1, the amount of use of the solvent is not particularly limited. However, 1 to 100 parts by mass of the solvent with respect to 1 part by mass of the carboxylate ester-containing phenolic compound is favorable from a viewpoint of the temperature control at the time of reaction or control of sub-reaction. In particular, with regard to the amount of use of the solvent, 1 to 10 parts by mass of the solvent with respect to 1 part by mass of the carboxylate ester-containing phenolic compound is more favorable in view of the economy. In the process A1, the reaction temperature is not particularly limited as long as it is higher than the freezing point of the solvent. However, it is favorably −20° C. to 50° C., which is easily controlled, and more favorably, −20° C. to 0° C. from a viewpoint of preventing sub-reaction from occurring.

Although the reaction time in the process A1 is not particularly limited, it can be normally 1 to 8 hours, in the process A1, the amount of use of COP is normally 0.7 to 3.0 molar equivalent, favorably 0.8 to 2.0 molar equivalent, and more favorably 0.9 to 1.2 molar equivalent, to 1 mole of the carboxylate ester-containing phenolic compound. Examples of the dehydrochlorination agent used in the process A1 include organic bases and inorganic bases. Further, the dehydrochlorination agent is favorably trimethylamine, triethylamine, diisopropylamine, pyridine, or the like from a viewpoint of the solubility to the solvent, the filterability of the generated salt, and the like.

The amount of use of the above-mentioned dehydrochlorination agent is normally 0.7 to 3.0 molar equivalent, favorably 0.8 to 2.0 molar equivalent, and more favorably 0.9 to 1.2 molar equivalent, to COP.

(Process A2)

The process A2 is a process in which a carboxylate ester-containing PC compound is generated by causing the carboxylate ester-containing OP compound obtained in the process A1 to react with trimethylamine. The process A2 can be performed in the presence of a solvent. As the solvent, a non-protic solvent is favorable. Examples of the non-protic solvent include nitriles such as acetonitrile, ketones such as acetone and methylethylketone, amides such as dimethylformamide, esters such as ethyl acetate and isopropyl acetate, ethers such as tetrahydrofuran, and chlorine-based organic solvents such as chloroform and dichloromethane. In the process A2, the amount of use of the solvent is not particularly limited. However, 1 to 100 parts by mass of the solvent with respect to 1 part by mass of the carboxylate ester-containing OP compound is favorable from a viewpoint of the temperature control at the time of reaction or control of sub-reaction. In particular, with regard to the amount of use of the solvent, 1 to 20 parts by mass of the solvent with respect to 1 part by mass of the carboxylate ester-containing OP compound is more favorable in view of the economy.

In the process A2, the reaction temperature is not particularly limited. However, it can be normally 40° C. to 80° C. Although the reaction time in the process A2 is not particularly limited, it can be normally 6 to 24 hours. In the process A2, the amount of use of trimethylamine is normally 1 to 2 molar equivalent to the carboxylate ester-containing OP compound.

(Process A3)

The process A3 is a process in which a carboxyl group-containing PC compound is synthesized by hydrolyzing the ester of the carboxylate ester-containing PC compound obtained in the process A2 in the presence of a basic compound in water. The process A3 can be performed in the presence of a solvent. The solvent is normally only water or an organic solvent containing water, and favorably only water. In the process A3, although the amount of use of the solvent is not particularly limited, 1 to 100 parts by mass of the solvent with respect to 1 part by mass of the carboxylate ester-containing PC compound is favorable from a viewpoint of the temperature control at the time of reaction or control of sub-reaction. In particular, with regard to the amount of use of the solvent, 1 to 20 parts by mass of the solvent with respect to 1 part by mass of the carboxylate ester-containing PC compound is more favorable in view of the economy.

The basic compound used in the process A3 is not particularly limited as long as it is capable of cutting the ester bond and converting it into a carboxyl group. Examples of the basic compound include a strong basic compound such as potassium hydroxide, sodium hydroxide, diazabicyclononene (DBN), diazabicycloundecene (DBU), and trimethylamine from a viewpoint of the reaction rate. The amount of use of the above-mentioned basic compound can be normally 1 to 2 molar equivalent to the carboxylase ester-containing PC compound. In the process A3, although the reaction temperature is not particularly limited, it can be normally 0° C. to 100° C. Although the reaction time in the process A3 is not particularly limited, it can be normally 1 to 6 hours.

<Manufacturing Method 2 for PC Group-Containing Compound>

A manufacturing method 2 for a PC group-containing compound specifically includes the following processes B1 to B3.

Process B1: By causing an alkyl group-containing phenolic compound and COP to react in a solvent by using a dehydrochlorination agent, an alkyl group-containing OP compound is generated.

Process B2: By causing the alkyl group-containing OP compound obtained in the process B1 to react with trimethylamine, an alkyl group-containing PC compound is generated.

Process B3: By oxidizing the alkyl group-containing PC compound obtained in the process B2 by using an oxidizing agent, a compound having a structure that contains a carboxyl group and is represented by the formula (1) is generated.

(Process B1)

The process B1 is a process in which an alkyl group-containing OP compound is generated by causing an alkyl group-containing phenolic compound and COP to react in a solvent by using a dehydrochlorination agent. As the above-mentioned alkyl group-containing phenolic compound, a compound having a structure in which one alkyl group is bonded to a benzene ring, such as cresol, can be used. In addition, any of ortho-, meta-, and para-positional isomers thereof can also be used.

The process B1 can be performed in the presence of a solvent. As the solvent, a non-protic solvent is favorable. Examples of the non-protic solvent include nitriles such as acetonitrile, ketones such as acetone and methylethylketone, amides such as dimethylformamide, esters such as ethyl acetate and isopropyl acetate, ethers such as tetrahydrofuran, and chlorine-based organic solvents such as chloroform and dichloromethane. In the process B1, the amount of use of the solvent is not particularly limited. However, 1 to 100 parts by mass of the solvent with respect to 1 part by mass of the alkyl group-containing phenolic compound is favorable from a viewpoint of the temperature control at the time of reaction or control of sub-reaction. In particular, with regard to the amount of use of the solvent, 1 to 100 parts by mass of the solvent with respect to 1 part by mass of the alkyl group-containing phenolic compound is more favorable in view of the economy.

In the process B1, the reaction temperature is not particularly limited as long as it is higher than the freezing point of the solvent. However, it is favorably −20° C. to 50° C., which is easily controlled, and more favorably, −20° C. to 0° C. from a viewpoint of preventing sub-reaction from occurring. Although the reaction time in the process B1 is not particularly limited, it can be normally 1 to 6 hours.

In the process B1, the amount of use of COP is normally 0.7 to 3.0 molar equivalent, favorably 0.8 to 2.0 molar equivalent, and more favorably 0.9 to 1.2 molar equivalent, to 1 mole of the alkyl group-containing phenolic compound. Examples of the dehydrochlorination agent used in the process B1 include organic bases and inorganic bases. Further, the dehydrochlorination agent is favorably trimethylamine, triethylamine, diisopropylamine, pyridine, or the like from a viewpoint of the solubility to the solvent, the filterability of the generated salt, and the like. The amount of use of the above-mentioned dehydrochlorination agent is normally 0.7 to 3.0 molar equivalent, favorably 0.8 to 2.0 molar equivalent, and more favorably 0.9 to 1.2 molar equivalent, to COP.

(Process B2)

The process B2 is a process in which an alkyl group-containing PC compound is generated by causing the alkyl group-containing OP compound obtained in the process B1 to react with trimethylamine. The process B2 can be performed in the presence of a solvent. As the solvent, a non-protic solvent is favorable. Examples of the non-protic solvent include nitriles such as acetonitrile, ketones such as acetone and methylethylketone, amides such as dimethylformamide, esters such as ethyl acetate and isopropyl acetate, ethers such as tetrahydrofuran, and chlorine-based organic solvents such as chloroform and dichloromethane. In the process B2, the amount of use of the solvent is not particularly limited. However, 1 to 100 parts by mass of the solvent with respect to 1 part by mass of the alkyl group-containing OP compound is favorable from a viewpoint of the temperature control at the time of reaction or control of sub-reaction. In particular, with regard to the amount of use of the solvent, 1 to 20 parts by mass of the solvent with respect to 1 part by mass of the alkyl group-containing OP compound is more favorable in view of the economy.

In the process B2, the reaction temperature is not particularly limited. However, it can be normally 40° C. to 80° C. Although the reaction time in the process B2 is not particularly limited, it can be normally 6 to 24 hours. In the process B2, the amount of use of trimethylamine is normally 1 to 2 molar equivalent to the alkyl group-containing OP compound.

(Process B3)

The process B3 is a process in which a carboxyl group-containing PC compound is produced by oxidizing the alkyl group-containing PC compound obtained in the process B2 by using an oxidizing agent. The process B3 can be performed in the presence of a solvent. The solvent is not particularly limited. However, it is favorably a protic solvent, and particularly, more favorably, water. In the process B3, although the amount of use of the solvent is not particularly limited, 1 to 100 parts by mass of the solvent with respect to 1 part by mass of the alkyl group-containing PC compound is favorable from a viewpoint of the temperature control at the time of reaction or control of sub-reaction. In particular, with regard to the amount of use of the solvent, 1 to 10 parts by mass of the solvent with respect to 1 part by mass of the alkyl group-containing PC compound is more favorable in view of the economy.

The oxidizing agent used in the process B3 is not particularly limited as long as it is capable of converting the alkyl group into a carboxyl group. The oxidizing agent is favorably a strong oxidizing agent such as permanganate from a viewpoint of the reaction rate, and more favorably potassium permanganate in view of the availability. The amount of use of the above-mentioned oxidizing agent is not particularly limited. However, it is favorably 1 to 10 molar equivalent, and more favorably 1 to 3 molar equivalent, to the alkyl group-containing PC compound in view of the economy and environmental burden.

In the process B3, although the reaction temperature is not particularly limited, it is favorable that the reaction is caused to proceed at the temperature of approximately the boiling point of the solvent under reflux, in view of the reaction rate. Although the reaction time in the process B3 is not particularly limited, it can be normally 1 to 8 hours.

The compound in which X is hydroxysuccinimide or N-hydroxysulfosuccinimide sodium salt, which have a structure represented by the formula (2), (hereinafter, abbreviated as NHS compound) is obtained by further performing the following process C on the carboxyl group-containing PC compound in which X is a carboxylic acid or salt obtained in the above.

(Process C)

The process C is a process in which the carboxyl group-containing PC compound (X is a carboxylic acid or salt) obtained in the process A3 or B3 and N-hydroxysuccinimide or N-hydroxysulfosuccinimide sodium salt are condensed by using a condensation agent to produce NHS compound. The process C can be performed in the presence of a solvent. As the solvent, a non-protic solvent is favorable. Examples of the non-protic solvent include nitriles such as acetonitrile and benzonitrile, ketones such as acetone and methylethylketone, amides such as dimethylformamide, sulfoxides such as dimethyl sulfoxide, esters such as ethyl acetate and isopropyl acetate, ethers such as tetrahydrofuran and 1,4-dioxane, and a chlorine-based organic solvent such as chloroform and dichloromethane. In particular, the solvent is favorably acetonitrile or dimethylformamide in view of the solubility and reaction rate.

In the process C, although the amount of use of the solvent is not particularly limited, 1 to 100 parts by mass of the solvent with respect to 1 part by mass of the carboxyl group-containing PC compound is favorable from a viewpoint of the temperature control and preventing sub-reaction from occurring. In particular, in view of the economy, with regard to the amount of use of the solvent, 1 to 10 parts by mass of the solvent with respect to 1 part by mass of the carboxyl group-containing PC compound is more favorable. In the process C, although the reaction temperature is not particularly limited, it can be normally 0° C. to 50° C. Although the reaction time in the process C is not particularly limited, it can be normally 8 to 96 hours.

Examples of the condensation agent used in the process C include 1-ethyl-3-(3-dimethylaminopropyl) carbodiimide hydrochloride, N,N'-diisopropylcarbodiimide, and 1,3-dicyclohexylcarbodiimide. In particular, in view of the economy, the condensation agent is favorably 1,3-dicyclohexylcarbodiimide.

The amount of use of the above-mentioned condensation agent can normally be 1 to 5 molar equivalent to the carboxyl group-containing PC compound. In the process C, the amount of use of N-hydroxysuccinimide or N-hydroxysulfosuccinimide sodium salt can be normally 1 to 5 molar equivalent to the carboxyl group-containing PC compound.

With the above-mentioned manufacturing method, it is possible to efficiently manufacture the PC group-containing compound according to the present invention.

3. Synthesis of PC Complex

By causing the phosphorylcholine group-containing compound according to the present invention to react with an amino acid amine site of a protein, peptide, or amino acid to form an amide bond, it is possible to obtain a phosphorylcholine-protein complex, a phosphorylcholine-peptide complex, or a phosphorylcholine-amino acid complex, respectively.

[Synthesis of PC-Protein Complex]

In the case where the PC group-containing compound according to the present disclosure is used to synthesize a PC-protein complex, human serum albumin (HSA), bovine serum albumin (BSA), egg white albumin (OVA), keyhole limpet hemocyanin (KLH), chicken gamma globulin (CGG), diphtheria toxoid, protein D, and the like can be used as a protein.

The reaction temperature, reaction time, and pH at the time when the PC-protein complex is synthesized are not particularly limited as long as the protein is not degraded or denatured. For example, the reaction temperature in the case where reaction is caused to proceed in an aqueous buffer solution under atmospheric pressure is normally 0° C. to 100° C., and favorably 20° C. to 60° C. The reaction time in this case is normally 1 second to 1 week, and favorably 1 hour to 3 days. Further, the pH in this case is normally 2 to 12, and favorably 5 to 9.

For purification of the PC-protein complex, a dialysis film can be used, for example. As the aqueous buffer solution used for synthesis and dialysis purification, an aqueous buffer solution used in a biochemical field, such as a phosphate buffer solution, a borate buffer solution, and a carbonate buffer solution, can be used. The salt concentration of the aqueous buffer solution is normally 0.0001 to 10 mol/L, and favorably 0.01 to 1 mol/L.

[Synthesis of PC-Peptide Complex]

In the case where the PC group-containing compound according to the present invention is used to synthesize a PC-peptide complex, an oligopeptide in which 2 to 10 amino acids including an arbitrary combination selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine are bonded together can be used as an oligopeptide.

The reaction temperature, reaction time, and pH at the time when the PC-peptide complex is synthesized are not particularly limited as long as the oligopeptide is not degraded or denatured. For example, the reaction temperature in the case where reaction is caused to proceed in an aqueous buffer solution under atmospheric pressure is normally 0° C. to 100° C., and favorably 20° C. to 60° C. The reaction time in this case is normally 1 second to 1 week, and favorably 1 hour to 3 days. Further, the pH in this case is normally 2 to 12, and favorably 5 to 9.

[Synthesis of PC-Amino Acid Complex]

In the case where the PC group-containing compound according to the present invention is used to synthesize a PC-amino acid complex, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine can be used as an amino acid.

Examples of the method of synthesizing the PC-amino acid complex include a method of causing a binding reaction to proceed in water or a buffer solution by using a condensation agent.

The above-mentioned condensation agent is not particularly limited. However, highly water-soluble ethyl dimethylaminopropyl carbodiimide hydrochloride can be used, for example.

The reaction temperature, reaction time, and pH at the time when the PC-amino acid complex is synthesized are not particularly limited as long as the amino acid is not degraded or denatured. For example, the reaction temperature in the case where reaction is caused to proceed in an aqueous buffer solution under atmospheric pressure is normally 0° C. to 100° C., and favorably 20° C. to 60° C. The reaction time in this case is normally 1 second to 1 week, and favorably 1 hour to 3 days. Further, the pH in this case is normally 2 to 12, and favorably 5 to 9.

The PC-amino acid complex can be used as a raw material for obtaining a PC-protein complex or a PC-peptide complex by bonding the PC-amino acid complex to another oligopeptide or protein.

EXAMPLE

Hereinafter, the present invention will be more specifically described with examples and comparative examples. However, the present invention is not limited to the scope of these examples. Note that various kinds of measurement in the examples were performed as follows.

(1) Method of Analyzing PC Group-Containing Compound

<$^1$H NMR Measurement>

"JNM-AL400" (trade name) manufactured by JEOL Ltd. was used, and measurement was performed under the conditions of solvent: $D_2O$, reference material: HOD, sample concentration: 10 mg/g, and number of times of integration: 32.

<$^{31}$P NMR Measurement>

"JNM-AL400" (tradename) manufactured by JEOL Ltd. was used, and measurement was performed under the conditions of solvent: $D_2O$, reference material: $H_3PO_4$, sample concentration: 10 mg/g, and number of times of integration: 32.

<Mass Analysis>

"Q-micro2695" (trade name) manufactured by Waters Co., Ltd. was used, and measurement was performed under the conditions of sample concentration: 100 ppm, detection mode: ESP+, capillary voltage: 3.54 V, cone voltage: 30 V, ion source heater: 120° C., and desolvation gas: 350° C.

<High Performance Liquid Chromatography (HPLC)>

"Atlantis 13 3 μm 4.6×100 mm" (trade name) manufactured by Waters Co., Ltd. was used as a column, and measurement was performed under the conditions of flow rate: 0.9 mL/min, temperature: 40° C., amount of sample injection: 10 μL, detection wavelength: 254 nm, mobile phase: 0.1 vol % trifluoroacetic acid-containing distilled water/0.1 vol % trifluoroacetic acid-containing acetonitrile, and gradient condition: distilled water/acetonitrile=100/0 (0 minute), 85/15 (0 to 20 minutes), and 85/15 (20 to 30 minutes).

<Measurement of Absorbance>

"SpectraMax M3" (trade name) manufactured by Molecular Devices, LLC. was used, and the absorbance of 450 nm ($OD_{450}$) was measured.

(2) Method of Manufacturing PC Group-Containing Compound and Synthesis of Complex Example a1-1

Synthesis of Carboxylate Ester-Containing PC Compound (Processes A1 and A2)

One hundred and sixty g of acetonitrile and 15 g of trimethylamine were added to 20 g of 4-methyl hydroxybenzoate, and they were dissolved and cooled to 0° C. After that, 21 g of COP was dropped thereinto. After the dropping was finished, reaction was caused to proceed at 0° C. for 5 hours, and the generated trimethylamine hydrochloride was removed by filtration. After 200 g of acetonitrile and 12 g of trimethylamine were added to the obtained filtrate, reaction was caused to proceed at 75° C. for 15 hours. After that, they were cooled to 60° C. and concentrated until the amount of solutions was approximately 200 ml while blowing nitrogen. After the concentration, the solution was cooled to 25° C., and the precipitated crystal was filtered and dried under reduced pressure. Accordingly, 35.2 g (yield 85%) of 4-methoxycarbonylphenyl phosphorylcholine having a structure represented by a formula (5) was obtained as a reaction intermediate.

[Chem. 10]

(5)

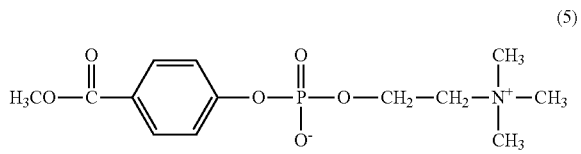

Figure 2:
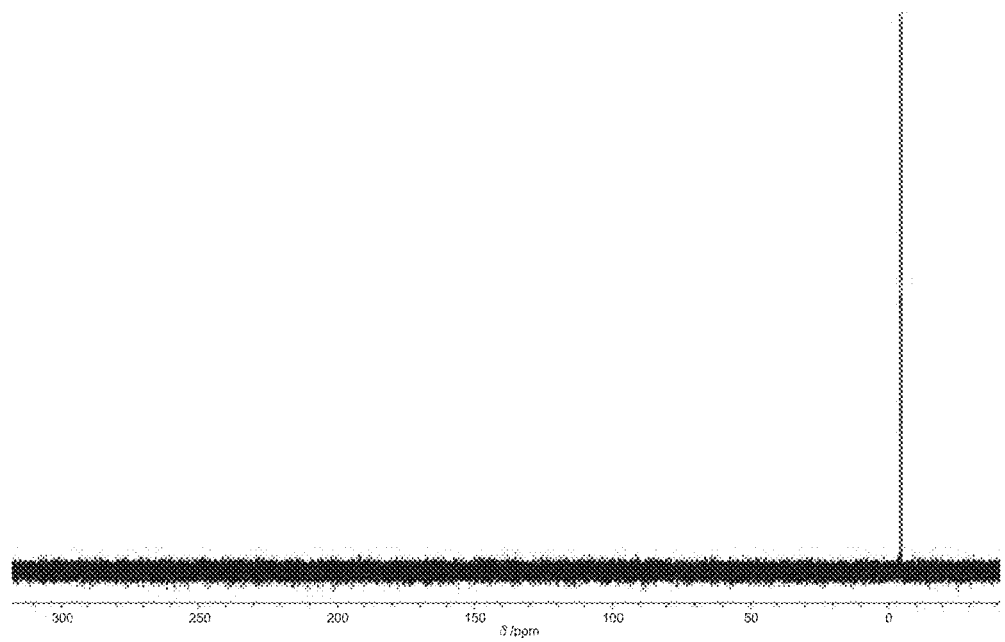
FIG. 2 A $^{31}$P NMR spectrum of 4-methoxycarbonylphenyl phosphorylcholine.
Figure 3:
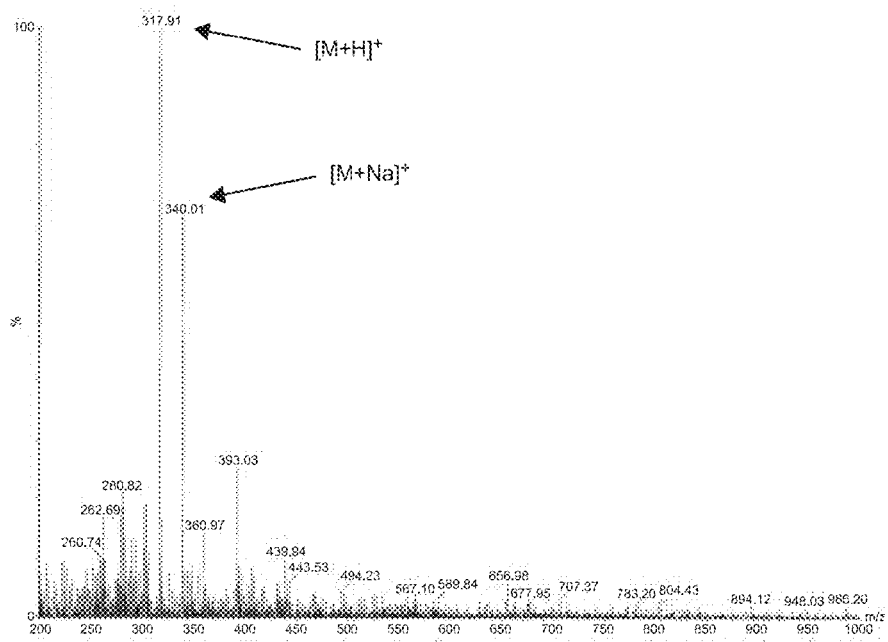
FIG. 3 An MS spectrum of 4-methoxycarbonyl phenyl phosphorylcholine.

FIG. 1 and FIG. 2 respectively show a $^1$H NMR spectrum and a $^{31}$P NMR spectrum of 4-methoxycarbonylphenyl phosphorylcholine obtained in the above. Further, FIG. 3 shows an MS spectrum of 4-methoxycarbonylphenyl phosphorylcholine obtained in the above.

The results of $^1$H NMR measurement, $^{31}$P NMR measurement, and mass analysis of the obtained product are as follows.

$^1$H NMR: δ=8.04 ppm (d, 2H, J=8.8: d), 7.30 ppm (d, 2H, J=8.8: e), 4.41 ppm (brs, c), 3.91 ppm (s, 3H: f), 3.68 ppm (m, 2H: b), 3.18 ppm (s, 9H: a)

$^{31}$P NMR: −4.59 ppm (t, J=15.9)

MS: [M+H]$^+$=317.91, [M+Na]$^+$=340.01

<Synthesis of 4-Carboxyphenyl Phosphorylcholine by Hydrolysis (Process A3, DBU Method)>

Ten g of 4-methoxycarbonylphenyl phosphorylcholine obtained in the above was dissolved in 90 g of distilled water, 5.0 g of DBU was added thereto, and they were stirred at 25° C. for 3 hours. After that, 3.6 g of concentrated hydrochloric acid was added thereto to neutralize the reaction solution, and the resulting solution was concentrated and dried by an evaporator. The obtained solid was recrystallized with 50 g of ethanol. Accordingly, 9.0 g (yield 94%) of the solid of 4-carboxyphenyl phosphorylcholine having a structure represented by a formula (6) was obtained.

[Chem. 11]

(6)

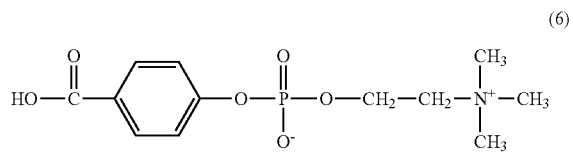

Figure 4:
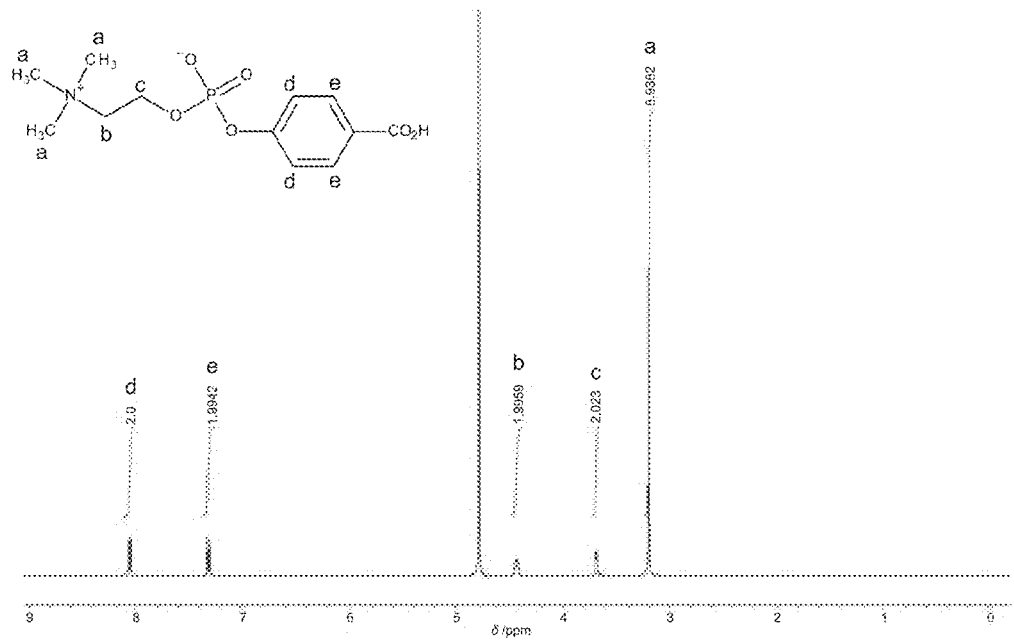
FIG. 4 A $^1$H NMR spectrum of 4-carboxyphenyl phosphorylcholine obtained by a DBU method.
Figure 5:
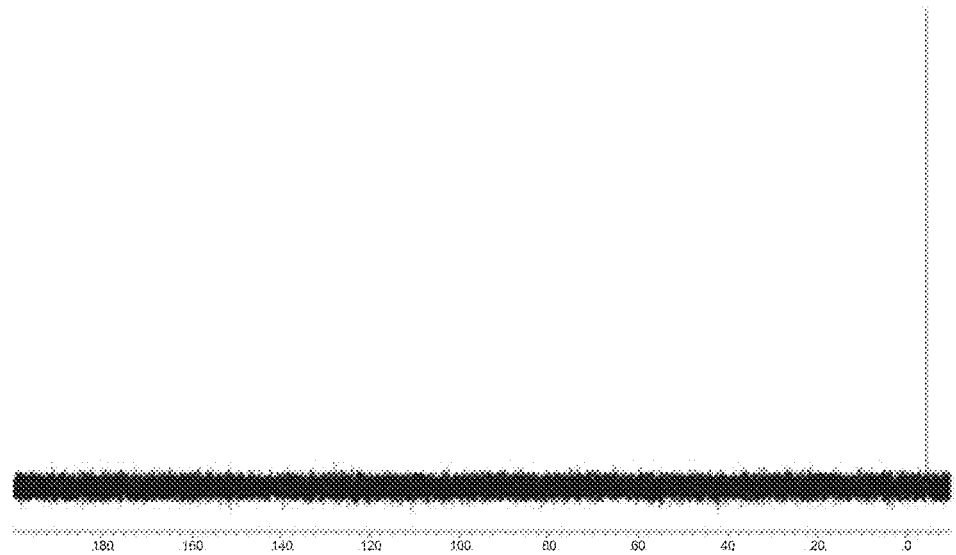
FIG. 5 A $^{31}$P NMR spectrum of 4-carboxyphenyl phosphorylcholine obtained by a DBU method.
Figure 6:
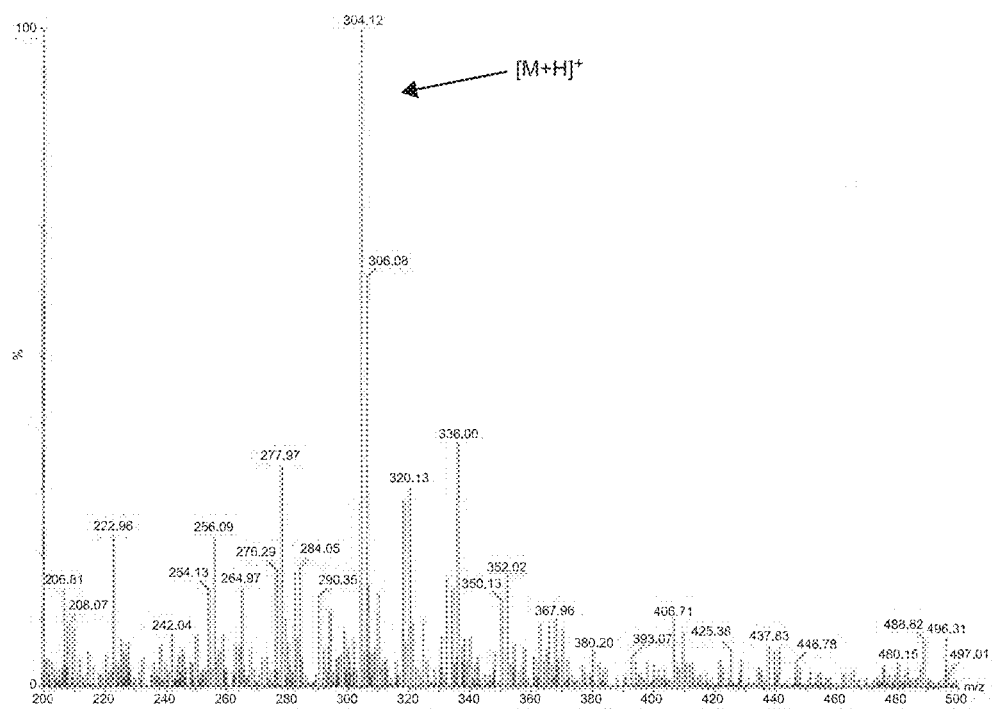
FIG. 6 An MS spectrum of 4-carboxyphenyl phosphorylcholine obtained by a DBU method.

FIG. 4 and FIG. 5 respectively show a $^1$H NMR spectrum and a $^{31}$P NMR spectrum of 4-carboxyphenyl phosphorylcholine obtained in the above. Further, FIG. 6 shows an MS spectrum of 4-carboxyphenyl phosphorylcholine obtained in the above.

The results of $^1$H NMR measurement, $^{31}$P NMR measurement, and mass analysis of the obtained product are as follows.

$^1$H NMR: δ=8.06 ppm (d, 2H, J=8.8: d), 7.33 ppm (d, 2H, J=8.8: e), 4.43 ppm (brs, 2H: b), 3.70 ppm (m, 2H: c), 3.19 ppm (s, 9H: a)

$^{31}$P NMR: −4.56 ppm (t, J=15.9)

MS: [M+H]$^+$=304.12

Example a1-2

Synthesis of 4-Carboxyphenyl Phosphorylcholine by Hydrolysis (Process A3, Trimethylamine Method)

Five g of 4-methoxycarbonylphenyl phosphorylcholine obtained in the above was dissolved in 45 g of distilled water, 3.19 g of trimethylamine was added thereto, and reaction was caused to proceed under reflux for 4 hours. After the reaction was finished, they were cooled to room temperature, 3.4 g of concentrated hydrochloric acid was added thereto to neutralize the reaction solution, and the resulting solution was concentrated under reduced pressure by a rotary evaporator. An operation of adding 50 g of 2-propanol and concentrating under reduced pressure was performed two times on the obtained residue, 50 g of 2-propanol was added thereto, and crystal was precipitated after stirring all night at −10° C. The solution was pressurized and filtered, and 4.0 g of the solid was obtained by drying the obtained crystal under reduced pressure.

$^1$H NMR measurement, $^{31}$P NMR measurement, and mass analysis were performed on the obtained product, and it was confirmed to be 4-carboxyphenyl phosphorylcholine (yield 84%). The results of $^1$H NMR measurement are as follows.

$^1$H NMR: δ=8.06 ppm (d, 2H, J=8.8), 7.33 ppm (d, 2H, J=8.8), 4.43 ppm (brs, 2H), 3.70 ppm (m, 2H), 3.19 ppm (s, 9H)

Example a1-3

Synthesis of 4-Carboxyphenyl Phosphorylcholine by Hydrolysis (Process A3, NaOH Method)

Ten g of 4-methoxycarbonylphenyl phosphorylcholine obtained in the above was dissolved in 90 g of distilled water, 1.2 g of sodium hydroxide was added thereto, and they were stirred at 2.5° C. for 2 hours. After that, 3.6 g of concentrated hydrochloric acid was added thereto to neutralize the reaction solution, and the resulting solution was concentrated and dried by an evaporator. After the obtained solid was column-purified, 8.5 g of the solid was obtained by evaporating the solvent.

$^1$H NMR measurement, $^{31}$P NMR measurement, and mass analysis of the obtained product were performed, and it was confirmed to be 4-carboxyphenyl phosphorylcholine (yield 88%). The results of $^1$H NMR measurement are as follows.

$^1$H NMR: δ=8.06 ppm (d, 2H, J=8.8), 7.33 ppm (d, 2H, J=8.8), 4.43 ppm (brs, 2H), 3.70 ppm (m, 2H), 3.19 ppm (s, 9H).

Example a1-4

Synthesis of Alkyl Group-Containing PC Compound (Processes B1 and B2)

One hundred g of acetonitrile and 22.5 g of diisopropylamine were added to 20.0 g of p-cresol, and they were dissolved and cooled to 0° C. After that, 31.6 g of COP was dropped thereinto. After the dropping was finished, reaction was caused to proceed at 0° C. for 3 hours, and the generated diisopropylamine hydrochloride was removed by filtration. One hundred g of acetonitrile and 16.4 g of trimethylamine were added to the obtained filtrate, and reaction was caused to proceed at 75° C. for 15 hours. After that, they were cooled to 60° C., concentrated until the amount of solutions was approximately 200 ml while blowing nitrogen, and cooled to 25° C. The precipitated crystal was filtered, washed with 100 g of acetonitrile, and then, filtered and dried under reduced pressure. Accordingly, 32.8 g of the solid of 4-methylphenyl phosphorylcholine having a structure represented by a formula (7) (yield 65%) was obtained as a reaction intermediate.

[Chem. 12]

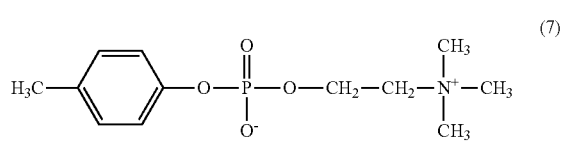

(7)

Figure 7:
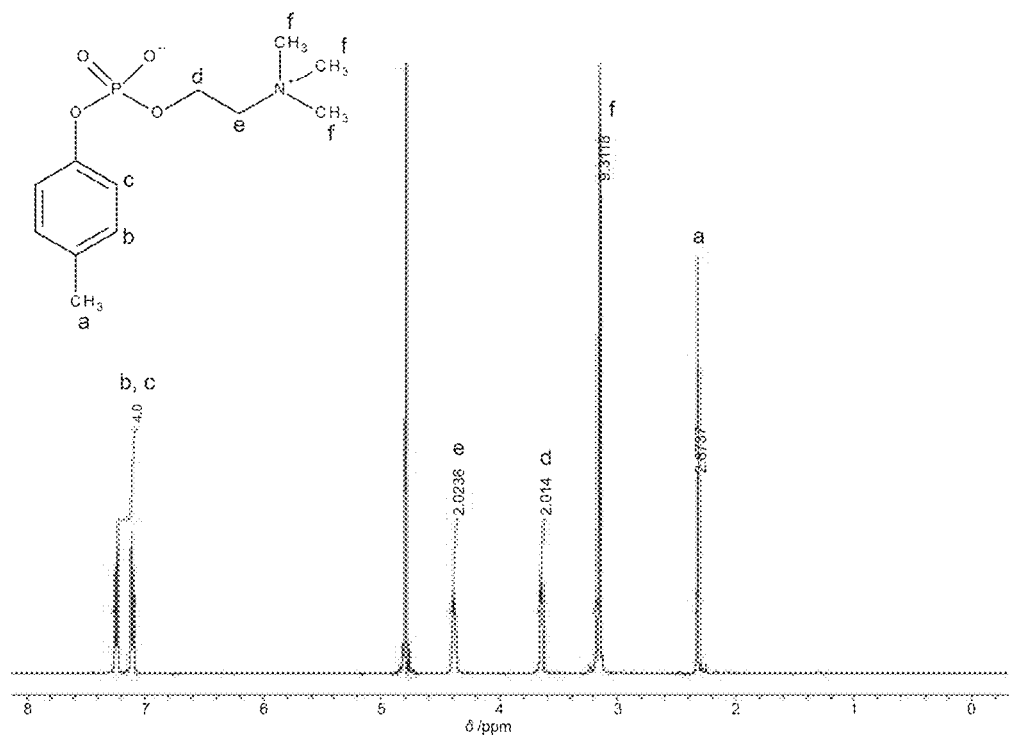
FIG. 7 A $^1$H NMR spectrum of 4-methylphenyl phosphorylcholine.
Figure 8:
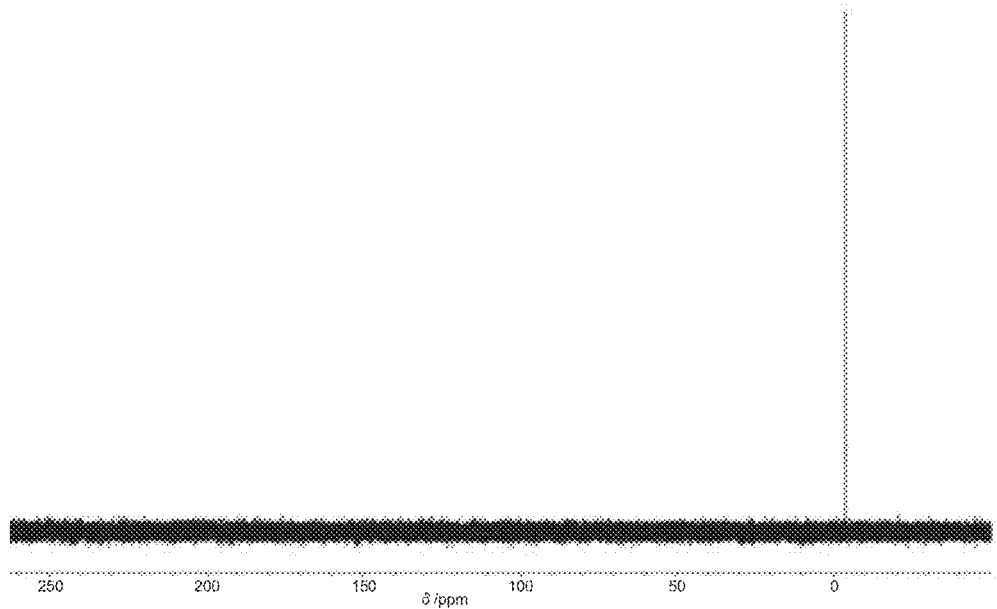
FIG. 8 A $^{31}$P NMR spectrum of 4-methylphenyl phosphorylcholine.
Figure 9:
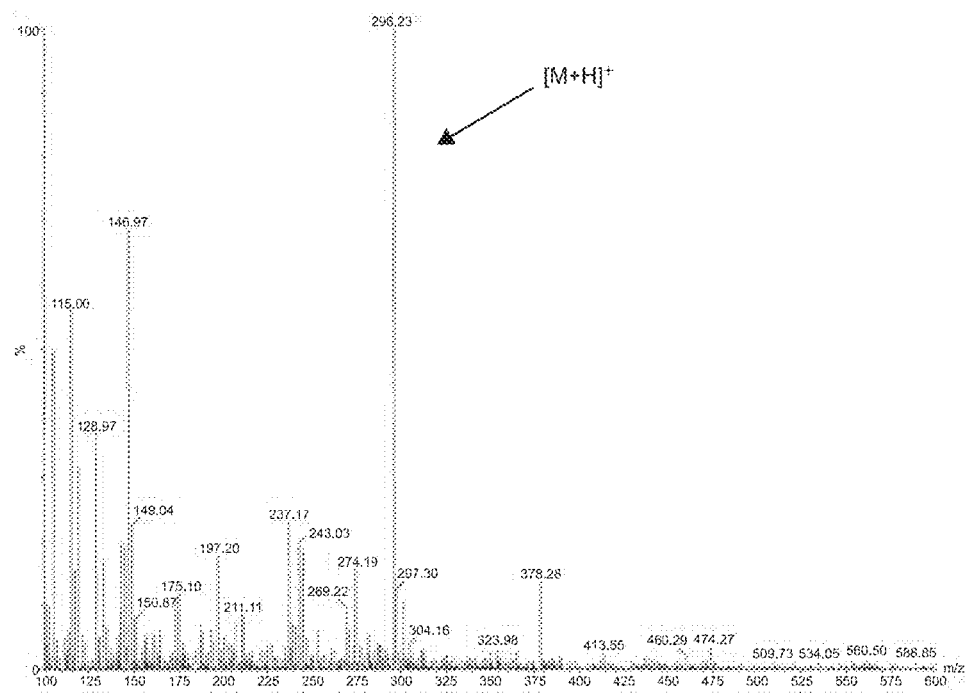
FIG. 9 An MS spectrum of 4-methylphenyl phosphorylcholine.

FIG. 7 and FIG. 8 respectively show a $^1$H NMR spectrum and a $^{31}$P NMR spectrum of 4-methylphenyl phosphorylcholine obtained in the above. Further, FIG. 9 shows an MS spectrum of 4-methylphenyl phosphorylcholine obtained in the above.

The results of $^1$H NMR measurement, $^{31}$P NMR measurement, and mass analysis of the obtained product are as follows.

$^1$H NMR: δ=7.25 ppm (d, 2H, J=7.8: b), 7.11 ppm (d, 2H, J=8.3: c), 4.38 ppm (brs, 2H: e), 3.65 ppm (m, 2H: d), 3.16 ppm (s, 9H: f), 2.32 ppm (s, 3H: a)

$^{31}$P NMR: −3.70 ppm (t, J=15.9)

MS: [M+H]$^+$=296.23

Synthesis of 4-Carboxyphenyl Phosphorylcholine by Oxidation (Process B3, Permanganate Method)

Five g of 4-methylphenyl phosphorylcholine obtained in the above was dissolved in 45 g of distilled water, and 6.1 g of potassium permanganate was added thereto. This solution was heated to 100° C., and reaction was caused to proceed under reflux for 3 hours. After it was cooled to 25° C., the insoluble matter was removed by filtration, and 4 g of hydrochloric acid of 35% was added to the obtained solution. After that, the solution was dried under reduced pressure by an evaporator, and after the column purification of the obtained solid, the solvent was evaporated. Accordingly, 4.4 g of the solid of 4-carboxyphenyl phosphorylcholine (yield 80%) was obtained.

Figure 10:
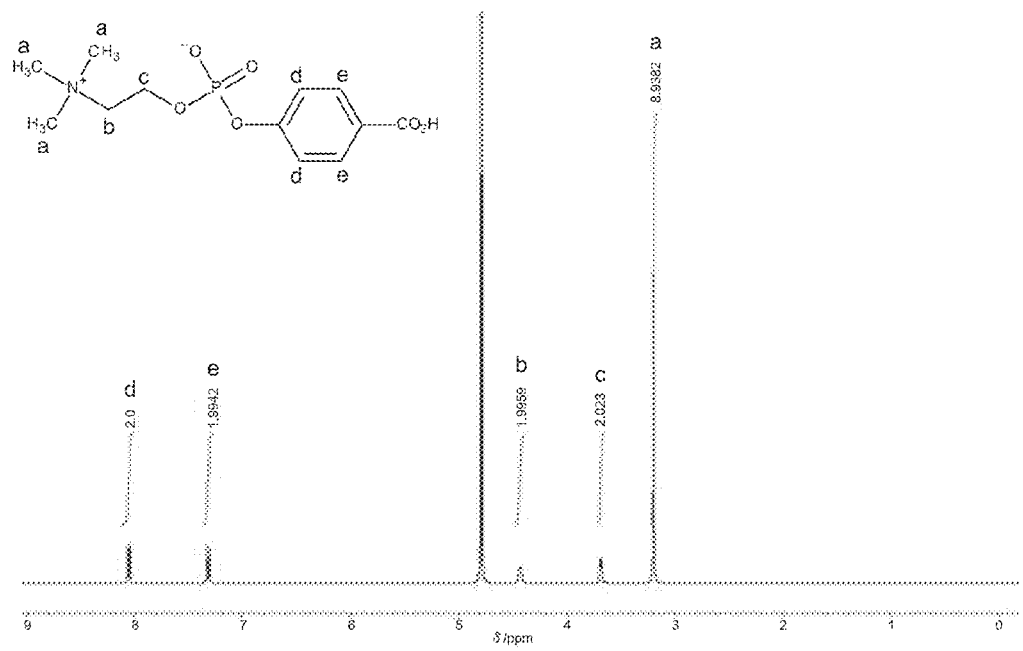
FIG. 10 A $^1$H NMR spectrum of 4-carboxyphenyl phosphorylcholine obtained by a permanganate method.
Figure 11:
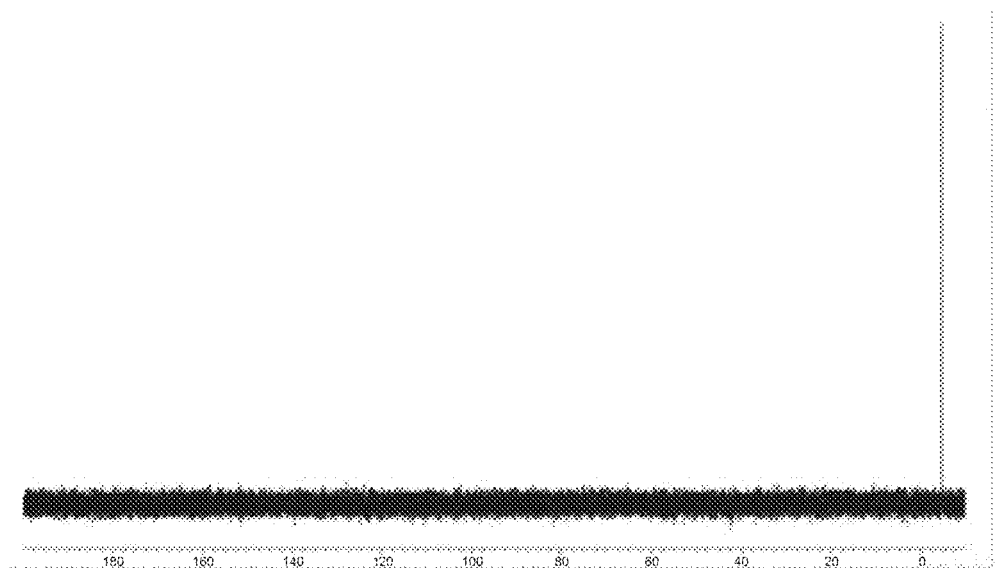
FIG. 11 A $^{31}$P NMR spectrum of 4-carboxyphenyl phosphorylcholine obtained by a permanganate method.
Figure 12:
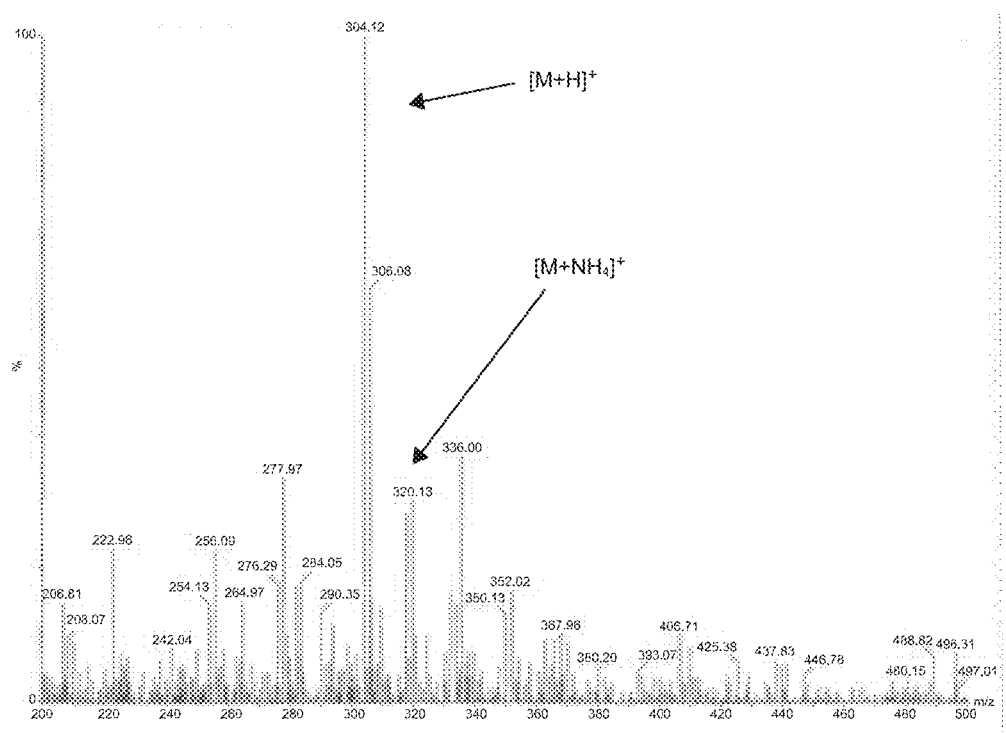
FIG. 12 An MS spectrum of 4-carboxyphenyl phosphorylcholine obtained by a permanganate method.

FIG. 10 and FIG. 11 respectively show $^1$H NMR spectrum and a $^{31}$P NMR spectrum of 4-carboxyphenyl phosphorylcholine obtained in the above. Further, FIG. 12 shows an MS spectrum of 4-carboxyphenyl phosphorylcholine obtained in the above.

The results of $^1$H NMR measurement, $^{31}$P NMR measurement, and mass analysis of the obtained product are as follows.

$^1$H NMR: δ=8.06 ppm (d, 2H, J=8.8: d), 7.33 ppm (d, 2H, J=8.8: e), 4.43 ppm (brs, b), 3.70 ppm (m, 2H: c), 3.19 ppm (s, 9H: a)

$^{31}$P NMR: −4.56 ppm (t, J=15.9)

MS: [M+H]$^+$=304.12, [M+NH$_4$]$^+$=320.13

Example a2-1

Synthesis of PC-Amino Acid Complex

First, morpholinoethanesulfonic acid hydrate (MES, manufactured by Sigma-Aldrich Co. LLC.) was dissolved in purified water to prepare a MES buffer solution of 0.1M. Next, 50 mg of 4-carboxyphenyl phosphorylcholine synthesized in the example a1-1, 50 mg of phenylalanine, and 25 mg of ethyl dimethylaminopropyl carbodiimide hydrochloride (manufactured by Pierce Biotechnologies, inc.) as a condensation agent were dissolved in 10 mL of MES buffer solution of 0.1M, and stirred at 25° C. for 24 hours. Accordingly, a PC-phenylalanine complex having a structure represented by a formula (8) was obtained.

[Chem. 13]

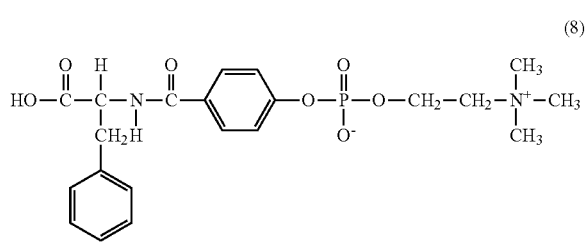

(8)

Figure 13:
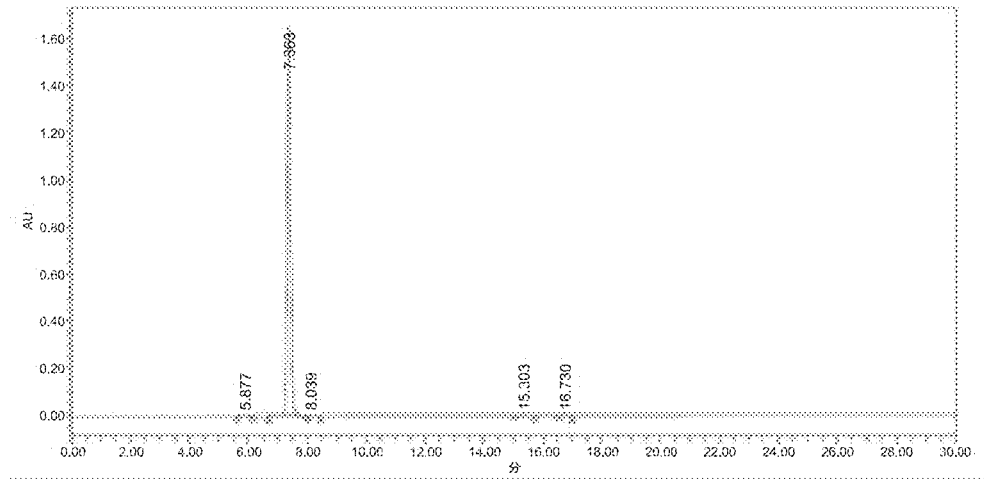
FIG. 13 An HPLC chromatogram before the reaction in synthesis of a PC-amino acid complex.
Figure 14:
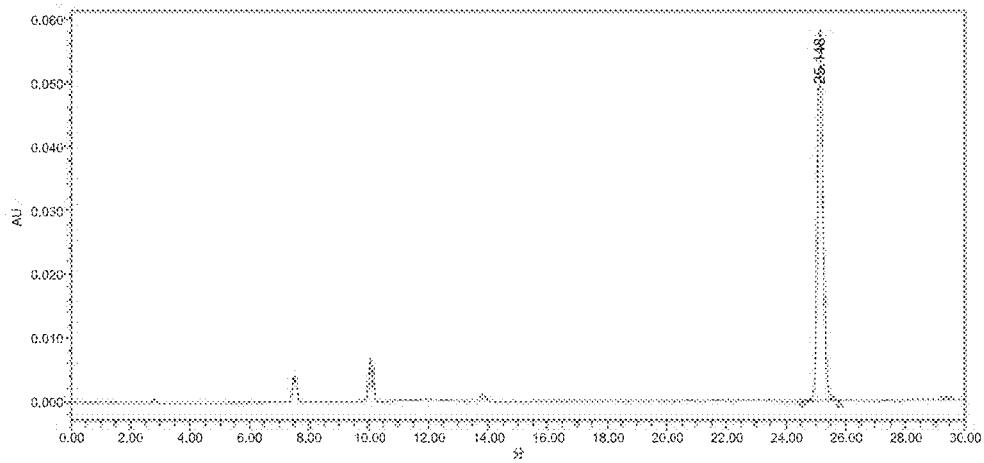
FIG. 14 An HPLC chromatogram after the reaction in synthesis of a PC-amino acid complex.
Figure 15:
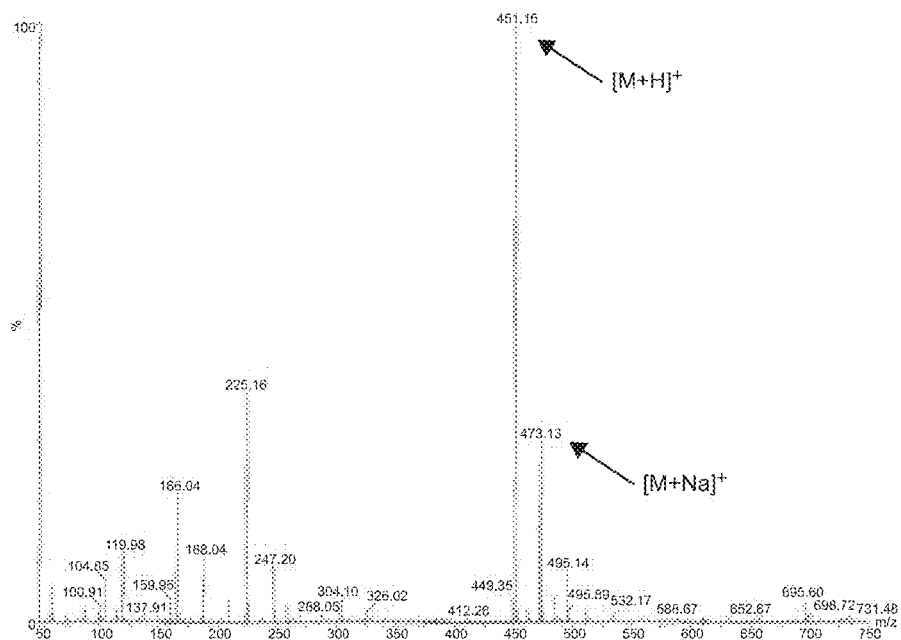
FIG. 15 An MS spectrum of a PC-phenylalanine complex.

FIG. 13 and FIG. 14 respectively show an HPLC chromatogram of the solution before stirring for 24 hours (before reaction) and an HPLC chromatogram of the solution after stirring for 24 hours (after reaction) in the synthesis of the above-mentioned PC-amino acid complex. In comparison with FIG. 13 and FIG. 14, it was confirmed that the peak of 4-carboxyphenyl phosphorylcholine disappeared, and a new peak appeared. FIG. 15 shows an MS spectrum of the product obtained in the above. From FIG. 15, the product was confirmed to be a PC-phenylalanine complex because a peak ([M+H]$^+$=451.16, [M+Na]$^+$=473.13) corresponding to the molecular weight of PC-phenylalanine complex was obtained.

Example a2-2

Synthesis of PC-Protein Complex

Four mg of 4-carboxyphenyl phosphorylcholine obtained in the example a1-1, 4 mg of bovine serum albumin (BSA, manufactured by Sigma-Aldrich Co. LLC.), and 2 mg of ethyl dimethylaminopropyl carbodiimide hydrochloride (Tokyo Chemical Industry Co., Ltd.) as a condensation agent were dissolved in 1.6 mL of MES buffer solution of 0.1M. After this solution was stirred at 2.5° C. for 2 hours, dialysis purification was performed at 4° C. in phosphate buffered saline (PBS) of pH 7.4. Accordingly, a PC-protein complex (PC-BSA) was obtained.

Example b1

Synthesis of 4-Carboxyphenyl Phosphorylcholine Succinimidyl (Process C)

Five point zero g of 4-carboxyphenyl phosphorylcholine obtained in the example a1-1 and 3.0 g of N-hydroxysuccinimide were suspended in 35 g of N,N-dimethylformamide (DMF). The temperature of this solution was maintained at 25° C., 6.8 g of 1,3-dicyclohexylcarbodiimide dissolved in 10 g of DMF was added thereto, and reaction was caused to proceed at 25° C. for 72 hours. After the reaction, the solution was filtered to collect a solid, and recrystallization was performed with 160 g of acetonitrile. After drying under reduced pressure, 4.5 g (yield 68%) of 4-carboxyphenyl phosphorylcholine succinimidyl having a structure represented by a formula (9) was obtained.

[Chem. 14]

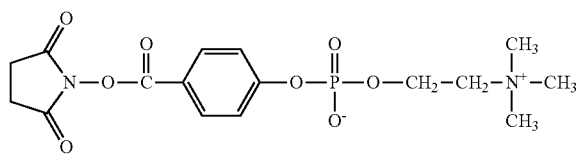

(9)

Figure 16:
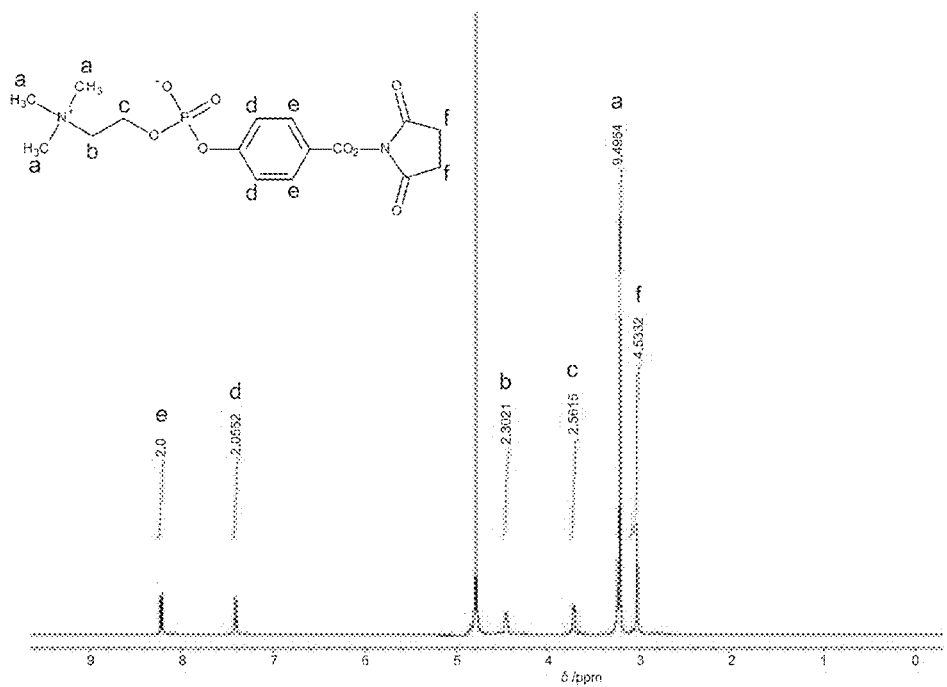
FIG. 16 A $^1$H NMR spectrum of 4-carboxyphenyl phosphorylcholine succinimidyl.
Figure 17:
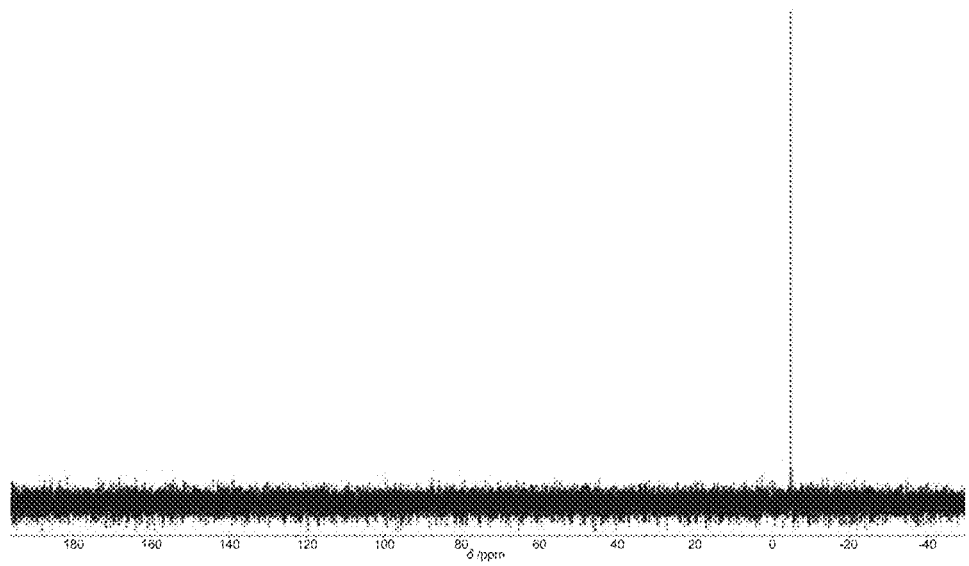
FIG. 17 A $^{31}$P NMR spectrum of 4-carboxyphenyl phosphorylcholine succinimidyl.
Figure 18:
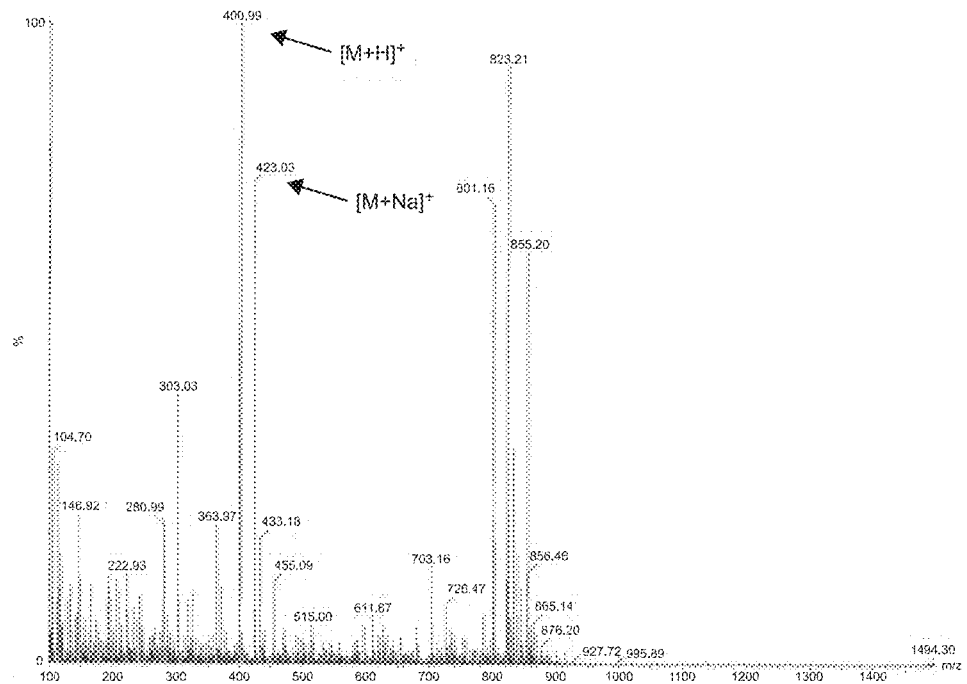
FIG. 18 An MS spectrum of 4-carboxyphenyl phosphorylcholine succinimidyl.

FIG. 16 and FIG. 17 respectively show a $^1$H NMR spectrum and a $^{31}$P NMR spectrum of 4-carboxyphenyl phosphorylcholine succinimidyl obtained in the above. Further, FIG. 18 shows an MS spectrum of 4-carboxyphenyl phosphorylcholine succinimidyl.

The results of $^1$H NMR measurement, $^{31}$P NMR measurement, and mass analysis of the obtained product are as follows.

1H NMR: δ=8.23 ppm (d, 2H, J=8.8: e), 7.42 ppm (d, 2H, J=8.3: d), 4.45 ppm (brs, 2H: b), 3.72 ppm (m, 2H: c), 3.22 ppm (s, 9H: a), 3.04 ppm (s, 4H: f)

$^{31}$P NMR: −4.96 ppm (t, J=15.9)

MS: [M+H]+=400.99, [M+Na]+=423.03

Example b2

Synthesis of PC-Protein Complex

Twenty mg of 4-carboxyphenyl phosphorylcholine succinimidyl obtained in the example b1, 8 mg of bovine serum albumin (BSA, manufactured by Sigma-Aldrich Co. LLC.), and 8 mg of sodium hydrogen carbonate were dissolved in 2 mL of distilled water. After this solution was stirred at 25° C. for 24 hours, dialysis purification was performed at 4° C. in phosphate buffered saline (PBS) of pH 7.4. Accordingly, a PC-protein complex (PC-BSA) was obtained.

(3) Evaluation of PC Group-Containing Compound

<Sample Preparation>

Saliva was collected from five healthy subjects in their twenties to forties, and a solution obtained by diluting the saliva 16-fold with Block Ace (manufactured by Sumitomo Dainippon Pharma Co., Ltd.) of 10% was used as a sample.

<Measurement of Anti-PC Antibody>

First, PC-BSA or BSA obtained in the above-mentioned example a2-2 or b2, respectively, was dissolved in a carbonate/bicarbonate buffer solution (manufactured by Sigma-Aldrich Co. LLC.), and the concentration thereof was adjusted to 5 μL/mL. Fifty μL/well of the resulting solution was dispensed in a 96-well microtiter plate (manufactured by DYNATEC CORP.), and the plate was held at 4° C. for 16 hours. Next, after PBS to which Tween20 of 0.05% was added was used to wash the plate, 200 μL/well of block ace of 25% was dispensed therein, and the plate was held at 36° C. for 1 hour. Next, PBS to which Tween20 with concentration of 0.05% was added was used to wash the plate, 50 μL/well of the sample was injected thereinto, and the plate was held at 25° C. for 1 hour. Next, PBS to which Tween20 with concentration of 0.05% was added was used to wash the plate, 50 μL/well of horseradish peroxidase (HRP)-labeled goat anti-human IgA antibody (manufactured by Southern Biotechnology Associates, Inc.) diluted 2000-fold was dispensed therein, and the plate was held at 25° C. for 1 hour. Next, PBS to which Tween20 with concentration of 0.05% was added was used to wash the plate, 100 μL/well of an HRP substrate solution was dispensed therein, and the reaction was caused to proceed at 25° C. for 15 minutes. After 15 minutes, 100 μL/well of dilute sulfuric acid was added thereto and the reaction was stopped. After that, the absorbance of 450 nm ($OD_{450}$) was measured.

<Method of Calculating Anti-PC Antibody Value>

The difference (anti-PC ($OD_{450}$) between the absorbance obtained from the plate on which PC-BSA was adsorbed (anti-PC-BSA ($OD_{450}$)) and the absorbance obtained from the plate on which BSA was adsorbed (anti-BSA ($OD_{450}$) as a negative control was calculated by using a formula (10). A calibration curve was created for each measurement, and an anti-PC antibody value (μg equal amount/mL) of each sample from the obtained value of the anti-PC ($OD_{450}$) was calculated.

anti-PC ($OD_{450}$)=anti-PC-BSA ($OD_{450}$)−anti-BSA ($OD_{450}$) (10)

<Measurement Result>

Table 1 shows the measurement results of an anti-PC antibody value of PC-BSA (example a2-2) according to a PC group-containing compound in which X is a hydrogen atom or a monovalent cation residue.

TABLE 1

| Subject number | 1 | 2 | 3 | 4 | 5 |
|---|---|---|---|---|---|
| Anti-PC antibody value (μg equal amount/mL) | 0.075 | 0.092 | 0.084 | 0.127 | 0.098 |

Table 2 shows the measurement results an anti-PC antibody value of PC-BSA (example b2) according to a PC group-containing compound in which X is a hydroxysuccinimide group.

TABLE 2

| Subject number | 1 | 2 | 3 | 4 | 5 |
|---|---|---|---|---|---|
| Anti-PC antibody value (μg equal amount/mL) | 0.094 | 0.112 | 0.075 | 0.087 | 0.088 |

From Tables 1 and 2, an anti-PC antibody valent was confirmed in any of the subjects. Accordingly, it became clear that PC-BSA used in this test functioned as a PC antigen. From the above-mentioned results, it become clear that the PC-protein complex using the PC group-containing compound according to the present invention was a water-soluble PC-protein complex suitable for use as a PC antigen because a cross-linking reaction did not occur between PC and a protein.

(4) Comparative Examples

Comparative Example a1

A comparative example a1 is a comparative example of the PC group-containing compound according to the present invention, in which X is a hydrogen atom or a monovalent cation residue.

In accordance with the method described in the specification of WO 2004/074298, a compound having a structure represented by a formula (11) was synthesized. Four mg of the obtained compound having a structure represented by a formula (11), 4 mg of bovine serum albumin (BSA, manufactured by Sigma-Aldrich Co. LLC.), and 2 mg of ethyl di methylaminopropyl carbodiimide hydrochloride (manufactured by Tokyo Chemical Industry Co., Ltd.) as a condensation agent were dissolved in 1.6 mL of a MES buffer solution of 0.1M. This solution was stirred at 25° C., and attempts were made to synthesize a PC-protein complex. However, the product was in gel form, and couldn't be dissolved in a MES buffer solution of 0.1M used for measurement of an anti-PC antibody value.

[Chem. 15]

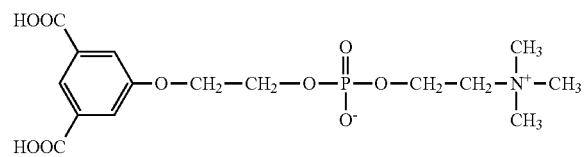

(11)

Comparative Example b1

A comparative example b1 is a comparative example of the PC group-containing compound according to the present disclosure, in which X is a hydroxysuccinimide group.

In accordance with the method described in the specification of WO 2004/074298, a compound having a structure represented by a formula (11) was synthesized. Twenty mg of the obtained compound having a structure represented by a formula (11), 8 mg of bovine serum albumin (BSA, manufactured by Sigma-Aldrich Co. LLC.), and 8 mg of sodium hydrogen carbonate were dissolved in 2 mL of distilled water. This solution was stirred at 2.5° C. for 24 hours. However, the product was in gel form, and couldn't be dissolved in a MES buffer solution of 0.1 M used for measurement of an anti-PC antibody value.

Comparative Example b2

A comparative example b2 is a comparative example of the PC group-containing compound according to the present invention, in which X is a hydroxysuccinimide group.

In accordance with the method described in the specification of WO 2004/074298, a compound having a structure represented by a formula (11) was synthesized. Five point zero g of the obtained compound having a structure represented by a formula (11) and 6.0 g of N-hydroxysuccinimide were added to 35.0 g of DMF. This solution was maintained at 25° C., 13.6 g of 1,3-dicyclohexylcarbodiimide dissolved in 20 g of DMF was added thereto, and reaction was caused to proceed at 25° C. for 72 hours. After the reaction, the solution was filtered to collect a solid, and recrystallization was performed with acetonitrile. After drying under reduced pressure, 4.4 g (yield 56%) of a compound having a structure represented by a formula (12) was obtained.

[Chem. 16]

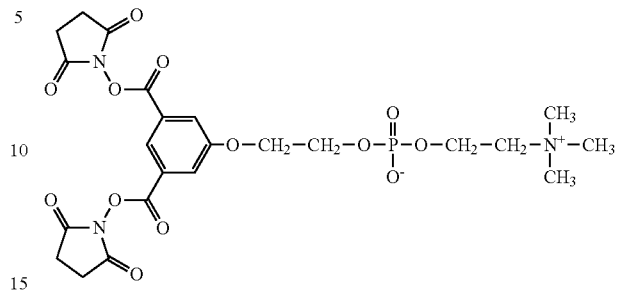

(12)

Twenty mg of the obtained compound having a structure represented by a formula (12), 8 mg of bovine serum albumin (BSA, manufactured by Sigma-Aldrich Co. LLC.), and 8 mg of sodium hydrogen carbonate were dissolved in 2 mL of distilled water. This solution was stirred at 25° C. for 24 hours. However, the product was in gel form, and couldn't be dissolved in a MES buffer solution of 0.1 M used for measurement of an anti-PC antibody value.

INDUSTRIAL APPLICABILITY

An aromatic compound having a structure that is represented by the formula (1) and includes one carboxyl group and a PC group can be effectively used as a raw material for obtaining a PC-protein complex. Further, the obtained PC-protein complex, PC-peptide complex, or PC-amino acid complex can be used as a PC antigen or a raw material for manufacturing a PC antigen. In addition, the obtained PC antigen can be effectively used a raw material for producing a PC antibody in manufacturing a pharmaceutical drug containing a PC antibody.

The invention claimed is:
1. A phosphorylcholine group-containing compound having a structure represented by the following formula (1)

[Chem. 1]

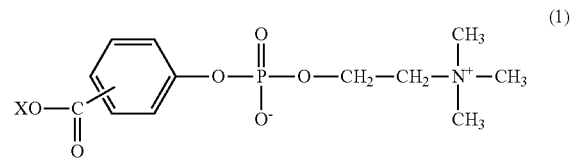

(1)

(X represents a hydrogen atom, a monovalent cation residue, or a structure represented by a formula (2))

[Chem. 2]

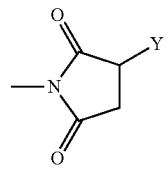

(2)

(Y represents a hydrogen atom or $SO_3Na$).

2. A phosphorylcholine-protein complex having a structure in which a phosphorylcholine group-containing compound having a structure represented by the following formula (1') and an amino acid amine site of a protein are amide bonded

[Chem. 3]

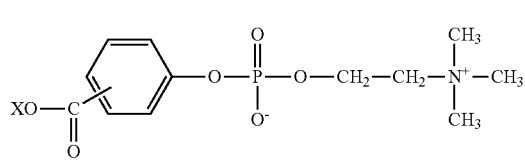
(1')

(X represents a hydrogen atom or a monovalent cation residue).

3. A phosphorylcholine-peptide complex having a structure in which a phosphorylcholine group-containing compound having a structure represented by the following formula (1') and an amino acid amine site of an oligopeptide are amide bonded

[Chem. 4]

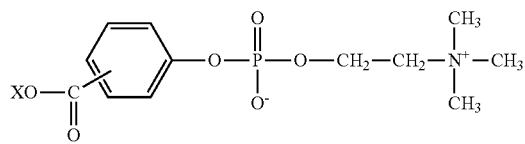
(1')

(X represents a hydrogen atom or a monovalent cation residue).

4. A phosphorylcholine-amino acid complex having a structure in which a phosphorylcholine group-containing compound having a structure represented by the following formula (1') and an amino acid amine site of an amino acid are amide bonded

[Chem. 5]

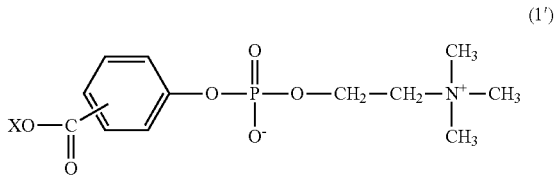
(1')

(X represents a hydrogen atom or a monovalent cation residue).

* * * * *